United States Patent [19]

Bradlow et al.

[11] Patent Number: 5,006,517

[45] Date of Patent: Apr. 9, 1991

[54] TREATMENT OF PRADER-WILLI SYNDROME

[75] Inventors: Leon Bradlow, Hollis Woods; Fred I. Chasalow, Glen Cove, both of N.Y.

[73] Assignees: Progenics, Inc., New York; Long Island Jewish Medical Center, New Hyde Park, both of N.Y.

[21] Appl. No.: 387,426

[22] Filed: Jul. 24, 1989

Related U.S. Application Data

[63] Continuation of Ser. No. 127,079, Dec. 1, 1987, abandoned.

[51] Int. Cl.⁵ .............................................. A61K 31/56
[52] U.S. Cl. ...................................... 514/178; 514/177; 514/909
[58] Field of Search ...................... 514/177, 178, 909

[56] References Cited

U.S. PATENT DOCUMENTS

| | | |
|---|---|---|
| 4,507,289 | 3/1985 | Coleman et al. .................... 514/170 |
| 4,518,595 | 5/1985 | Coleman et al. .................... 514/178 |
| 4,602,008 | 7/1986 | Krsek .................................. 514/178 |
| 4,666,898 | 5/1987 | Coleman et al. .................... 514/177 |

OTHER PUBLICATIONS

"Steroid Metabolic Disturbances in Prader-Willi Syndrome" by Fred I. Chasalow et al., American Journal of Medical Genetics, 28:857-864 (1987).

"Prader-Willi Syndrome Scientific Conference III Abstracts", by Bryan D. Hall et al., Clinical Genetics 1989: 35: 299-309.

"Fourth Annual Prader-Willi Syndrome Scientific Conference" Jul. 19, 1989, In Alberta, Canada.

*Primary Examiner*—Jerome D. Goldberg
*Assistant Examiner*—Terry L. Wilson

[57] ABSTRACT

Prader-Willi Syndrome is alleviated by administering of a 3-oxo or hydroxy substituted 5-beta-androstan-17-one to an individual having the syndrome.

12 Claims, 2 Drawing Sheets

TREATMENT OF PRADER-WILLI SYNDROME

This is a Continuation of application Ser. No. 07/127,079 filed on Dec. 1, 1987, now abandoned.

BACKGROUND OF THE INVENTION

One of the five most common problems seen in birth defect clinics today is Prader-Willi Syndrome. Among the characteristics of this syndrome are mental deficiency, short stature, marked obesity and sexual infantilism. Prader-Willi Syndrome often starts to become manifest during the first year of life but is difficult to diagnose because, except for an overwhelming hyperphagia which becomes the dominant symptom with time, the symptoms of the disease are very indeterminate. As a result, the initiation of remedial training (to overcome the mental retardation) and a drastic weight control program (required to combat the massive, compulsive and life-threatening overeating) is frequently delayed beyond the time that they should be initiated.

Prader-Willi Syndrome is a complex syndrome of unknown origin. The genetic role in the disease has been difficult to study since individuals suffering with the syndrome do not reproduce and frequently die during their early twenties. Nevertheless, it appears clear that the condition is not sex linked and has a low recurrence rate of not greater than 1%. It has been observed that approximately 50% of Prader-Willi cases exhibit a defect in the 15q region of chromosome 15 but this defect is also present in a few individuals without Praeder-Willi Syndrome. There are no specific biochemical tests which exist at the present in order to diagnose the syndrome. That fact, coupled with the indeterminate symptoms, frequently delays diagnosis. Further, once diagnosed, only palliative treatment of the symptoms is available to the physician.

The present invention is based on a discovery which resulted from an examination of the steroid sulfate profile of children suffering with Prader-Willi Syndrome and which demonstrated the presence of two characteristic metabolic patterns. In one group, dehydroepiandrosterone sulfate was the only sulfo-conjugate peak detected and, in the second, the DHEA-sulfate was accompanied by four other more polar sulfo-conjugate peaks. Based on this evidence, it was recognized that one of three etiologies could be involved, namely, 1.) low DHEA sulfate levels in the plasma due to a defect in one of the early steps in the biosynthetic pathway, 2.) excessive amounts of DHEA-sulfate metabolites associated with either a receptor or post-receptor defect, and 3.) excessive amounts of some DHEA-sulfate metabolites caused by a metabolic block in the pathway and consequent accumulation of other products. Further conformation of the existence of a steroidogenic defect comes from our recent observations that plasma etiocholanolone levels are low in patients with Praeder-Willi Syndrome. Thus, these data are consistent with a defect in the pathway leading to etiocholanolone synthesis. lone and certain of related compounds to eliminate this deficiency in individuals suffering with the syndrome. The consequence of relieving the deficiency is also advantageous in effecting weight loss or at least decreasing the rate of weight gain.

The steroid dehydroepiandrosterone (3-beta-hydroxyandrost-5-en-17-one, DHEA) and its sulfate derivatives are major steroid adrenal secretory products in humans. DHEA is metabolized to testosterone (17-beta-hydroxy-androst-4-en-3-one) and estradiol (estra-1, 3, 5 (10)-triene-3, 17-diol), two major sex hormones in humans. Other metabolites of DHEA include alpha-etiocholanolone (5-beta-androstan-3-alpha-ol-17-one, hereinafter referred to as alpha-ET) and beta-etiocholanolone (5-beta-androstan-3-beta-ol-17-one, hereinafter referred to as beta-ET) and were, until recently, considered to be inert metabolic end products which were merely conjugated as glucuronides or sulfates and excreted in the urine. Alpha-ET is a major metabolite of DHEA, and in normal individuals, is excreted in the urine in amounts of about 3-5 mg per day, whereas beta-ET is a minor metabolite in man.

Yen, et al. (*Lipids* 12:409, 1977) disclosed that DHEA, administered by a variety of routes, decreased the rate of weight gain in a strain of genetically obese mice. Coleman, et al. (*Diabetes* 31:830, 1982) demonstrated that DHEA treatment had a marked preventive effect on the development of diabetes in either genetically obese or diabetic mice. Furthermore, they indicated that for the maximal beneficial effect, DHEA had to be ingested. Coleman, et al. (*Endocrinology* 115:239-243, 1984) disclosed that alpha-ET and beta-ET, but not androsterone or epiandrosterone, were four time more effective than DHEA in preventing the development of diabetes in C57BL/KsJ-db/db diabetic mice. Alpha-ET and beta-ET reduced blood sugar, increased plasma insulin concentrations and provided a protective effect on the pancreas, as shown by an increase in the number of granules in the islet betacells. These results demonstrated that both compounds had physiological significance and were not merely end products of sterol metabolism.

Coleman, et al. (U.S. Pat. No. 4,518,595, incorporated by reference) disclosed that oral administration of DHEA restored hyperglycemia to normal levels and improved glucose tolerance even in severely diabetic mammals. Coleman, et al. (U.S. Pat. No. 4,507,289, incorporated by reference) taught the use of alpha- and/or beta-ET and an estrogen for the treatment of diabetes, obesity syndromes and associated hypercorticoidism. The activity of alpha-ET and beta-ET suggests that DHEA may actually be exerting its effects through its metabolites. The advantage of both alpha-ET and beta-ET over DHEA is that they cannot be converted to estradiol or testoserone.

Coleman (*Endocrinology* 117:2279-2283, 1985) disclosed that alpha-ET and beta-ET, when supplied in the diet, have anti-obesity properties. They were effective both in preventing and in arresting the development of obesity as well as in facilitating weight reduction after obesity and this has been established in diabetic, genetically obese mice. Finally, in U.S. Pat. No. 4,666,898 (incorporated herein by reference) Coleman and Applezweig disclose the use of etiocholanolones for the treatment of obesity, diabetes and other symptoms of hypercorticoidism.

It was discovered that alpha-ET and beta-ET administered orally, parenterally i.p., i.m. or i.v. are both rapidly oxidized at the C-3 position to form etiocholanedione (5-beta-androstanedione, hereinafter referred to as ET-dione) and that ET-dione can serve as a superior source of circulating blood levels of free (nonconjugated) alpha-ET. Once formed, the ET-dione is reduced only to alpha-ET, which may then be conjugated and excreted. This dynamic interconversion of alpha-ET and ET-dione provides the means of achieving alpha-ET blood levels through the use of ET-dione serving as a pro-drug for alpha-ET. In addition, whereas conjugation and excretion rapidly removes alpha-ET from the blood stream, ET-dione must be reduced to alpha-ET before being eliminated from the body, and may therefore have a longer circulatory half-life than alpha-ET. Animal and human pharmacokinetic data demonstrate that ET-dione produces increased blood levels of free alpha-ET. This increased blood level may be due to improved absorption of ET-dione over alpha-ET. This is the subject of U.S. application Ser. No. 078,610, filed July 28, 1987 and incorporated herein by reference.

The evidence referred to above and described in more detail below provides the missing suggestion. The accumulation of unidentified steroid sulfates in some serum from Prader-Willi Syndrome children is an indicator that there is a blocked biosynthetic pathway. No enzyme deficiency state has previously been associated with this syndrome. Adrenal steroid levels had previously been reported as normal and this is the first discovery of a decreased serum level for known steroids. Our evidence indicates individuals with Prader-Willi Syndrome have an enzyme deficiency syndrome of unknown parameters which causes a defect in a steroid biosynthetic pathway which apparently leads to a block in etiocholanolone synthesis, which in turn contributes to obesity.

It is accordingly the object of this invention to provide a method for correcting a steroid deficiency in an individual having Prader-Willi Syndrome. This and other objects of the invention will become apparent to those of ordinary skill in this art from the followed detailed description in which.

SUMMARY OF THE INVENTION

This invention relates to a method of correcting a steroid deficiency preferably which will result in causing either weight loss or at least a decrease in the rate of weight gain, in an individual having Prader-Willi Syndrome. More particularly, the invention relates to a method of supplying the missing steroid to an individual having Prader-Willi Syndrome by administering to that individual an effective amount of a 3-oxo or hydroxy substituted 5-beta-androstan-17-one.

DESCRIPTION OF THE INVENTION

The steroid sulfate profile of children having Prader-Willi Syndrome which led to the present invention was determined as follows. Steroid sulfates were separated from serum samples from seventeen children by extraction with methanol and chromatography on Sephasorb HP column using methanol: water (1:1) as eluant. This procedure separated these serum steroids into three fractions: glycosides, sulfates and neutral steroids. In order to identify the steroids present as sulfo-conjugates, the steroid sulfate peak fractions were pooled, lyophilized, hydrolyzed with Glusalase, extracted with ethyl acetate and chromatographed on a Sephadex LH-20 column using iso-octane:ethyl acetate: methanol (4:1:1) as the eluant. The column fractions were assayed for dehydroepiandrosterone-like steroids by radioimmunoassay. In newborn infants, it was found that there were four steroids (dehydroepiandrosterone, 16-alpha-hydroxy-dehydroepiandrosterone and 2 other polyhydroxylated 5-androstenes) present in the hydrolysate from the steroid sulfate fraction. In children of six months of age, this pattern had changed to one with little or no steroid conjugates present in the serum. In post-pubertal normal individuals, the main steroid conjugate is dehydroepiandrosterone sulfate.

The chromagraphic patterns of the steroid sulfate hydrolysates observed in patients with Prader-Willi Syndrome could be divided into two groups. Ten (four with the deletion on chromosome 15 and six without) of the seventeen individuals had a normal pattern with dehydroepiandrosterone as the only steroid detected. However, seven out of seventeen (three with the deletion and four without) had a very different pattern with five major peaks. This pattern of steroids is unique to Prader-Willi Syndrome and was not observed in the hydrolysates from obese children (n=5), hirsute women (n=5), girls with premature adrenarche (n=10), children with etiopathic delayed puberty (n=5) and many other normal individuals (n=40).

Figure 1:
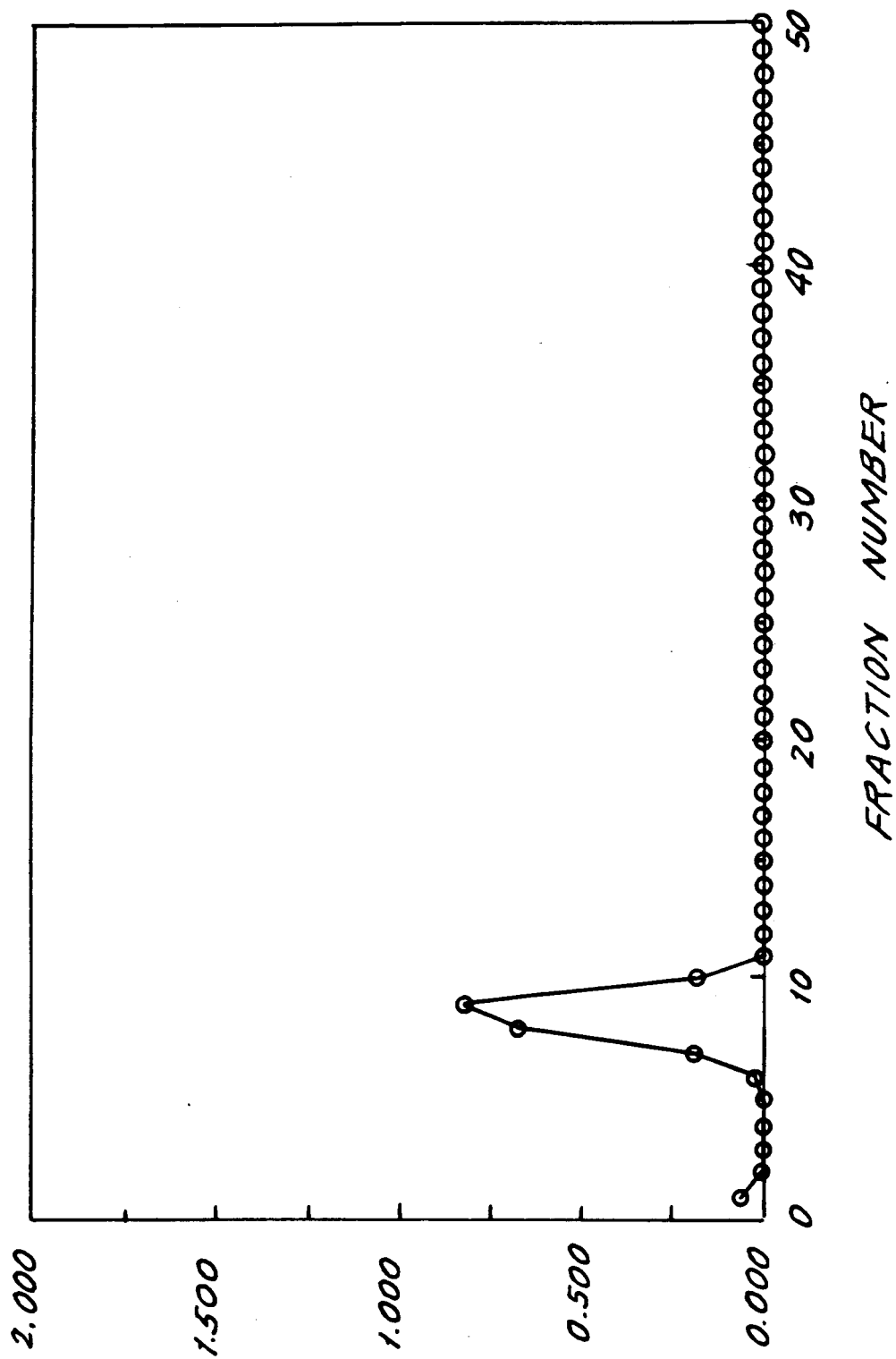
FIG. 1 is a chromatogram of sulfo-conjugates in group I patients.
Figure 2:
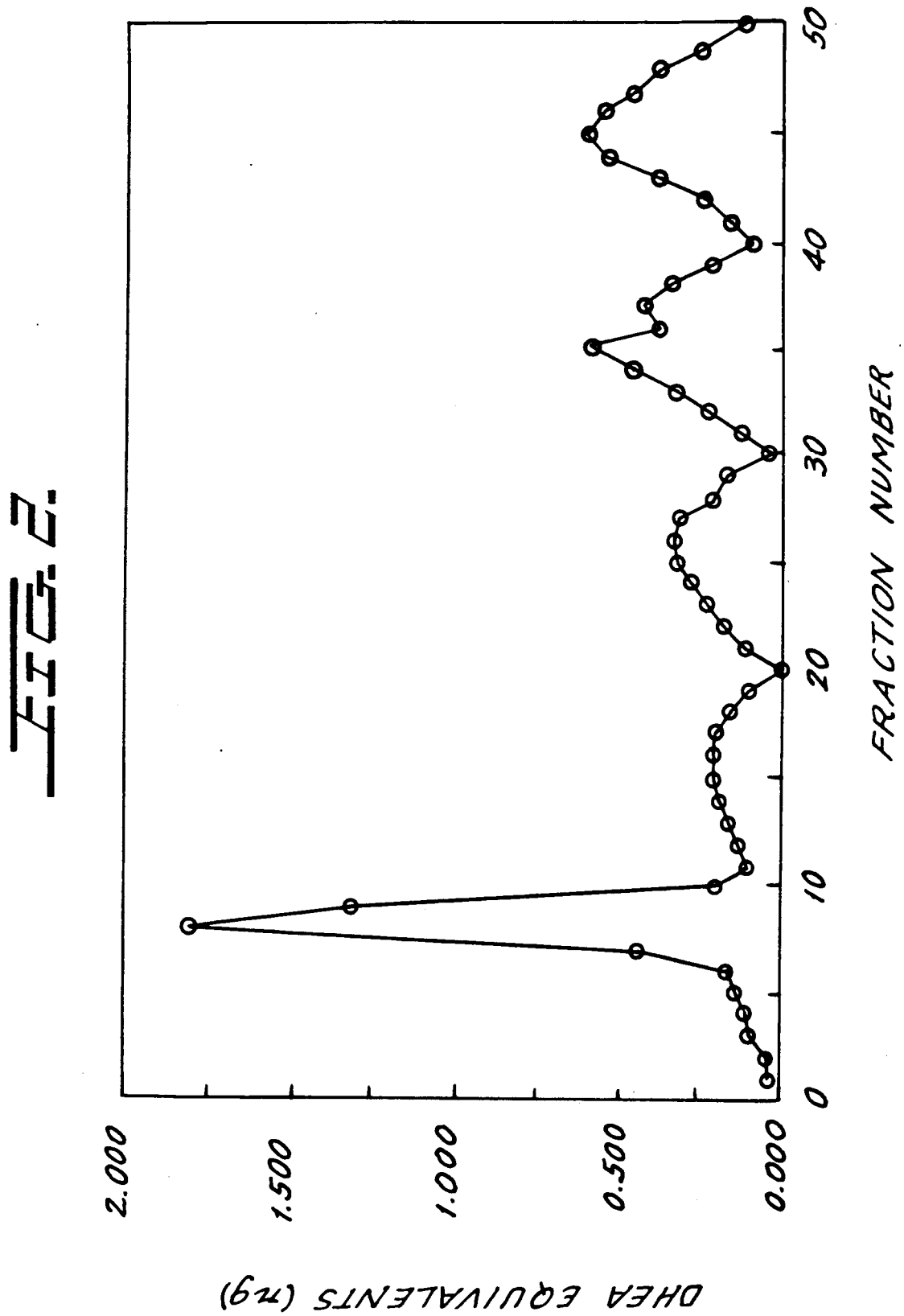
FIG. 2 is a chromatogram of sulfo-conjugates in group II patients.

Two representative chromatograms are set forth as FIGS. 1 and 2 to this application.

The results of these studies led to the recognition of a steroid biosynthetic defect in Prader-Willi Syndrome and thereby to the use of etiocholanolone and certain related compounds in the treatment of Prader-Willi Syndrome in order to ameliorate consequences of the defect, such as compulsive overeating.

The active agent used in this invention is a 3-hydroxy or oxo substituted 5-beta-androstan-17-one, that is ET-dione, alpha-ET or beta-ET. It will be recognized that the active agents can be utilized alone or in combination, as desired.

ET-dione is preferred because alpha-ET or beta-ET administered either orally or parenterally is rapidly oxidized at the C-3 position to ET-dione. Following conversion to the dione, the dione is reconverted to alpha-ET. The dione is absorbed rapidly and circulates in the blood for a longer period of time than does alpha-ET since it is not subject to rapid conjugation and excretion in the urine. Its only access to excretion would be by reconversion to alpha-ET and conjugation. Thus, ET-dione serves as a pro-drug for the maintenance of alpha-ET blood levels.

The reconversion of the dione to alpha-ET has been confirmed by administration of oral dosages of ET-dione by admixture with the diet (0.367%) over a period of three weeks to rats. The radioimmunoassay (RIA) values for alpha-ET rose from approximately 40 nanograms per deciliter to approximately 600 nanograms per deciliter at the end of the three week feeding program. In humans, it has been found that oral dosages of ET-dione lead to significantly enhanced blood levels of alpha-ET over equivalent dosages of alpha-ET (Table 1). In addition, ET-dione costs approximately one-third of what alpha-ET costs and is equally or, in some cases, almost twice as effective. All of the above considerations make ET-dione not only suitable but preferred in the treatment of Prader-Willi Syndrome.

Compositions containing the active agent are administered either orally or parenterally. When administered orally, the agent and compositions containing the agent can be administered in a finely dispersed powder or solution which can be mixed with the food diet, or alternatively can be administered in tablet form. Compositions for i.p. injection generally comprise serum albumin, propylene glycol and other wellknown agents as diluents and/or carriers. Average content of the active agent present in the compositions broadly ranges between about 1 and 1000 mg and preferably between about 10 and 500 mg per dosage form.

Average daily dosages broadly range between about 0.1 to about 100 mg/kg, and preferably between about 1 and about 10 mg/kg body weight for ET-dione and between about 1 and about 10 mg/kg for alpha-ET. The actual dose utilized is, as with all pharmaceuticals, best determined by the attending clinician for bringing etiocholanolone plasma levels into the range normally found in healthy individuals.

In the experiments described below, alpha-ET, beta-ET and ET-dione were obtained from Steraloids (Wilton, NH) or alternatively could have been purchased from Houba (Culver, IN) or Chemodynamics (Garfield, NJ).

The absorption and blood level profiles of alpha-ET, beta-ET and ET-dione administered as oral suspensions to eight normal human volunteers were studied in a three-way crossover design study. Each subject received all three drugs in randomized order with a one-week wash-out period between doses. Following an overnight fast, subjects received 200 mg of test drug suspended in approximately 6 oz. of apple juice. Blood samples were drawn immediately prior to drug administration and at 15 minutes, 30 minutes, 1, 2, 4, 8, 12 and 24 hours. Serum was obtained and analyzed for the level of alpha-ET by radioimmunoassay using antibodies commercially available from InterSci Diagnostics (Los Angeles, CA). The data is summarized in Table 1 below.

TABLE 1
FREE ALPHA-ET BLOOD LEVELS FROM ORAL ADMINISTRATION OF ALPHA-ET, BETA-ET AND ET-DIONE SUSPENSIONS

|  | Time (Hr.) | Alpha-ET Blood Level, ng/dl (Mean) |
|---|---|---|
| ALPHA-ET | 0 | 21.5 |
|  | 0.25 | 2044 |
|  | 0.5 | 1915 |
|  | 1 | 1234 |
|  | 2 | 526 |
|  | 4 | 183 |
|  | 8 | 91 |
|  | 12 | 44 |
|  | 24 | 25 |
| BETA-ET | 0 | 16 |
|  | 0.25 | 604 |
|  | 0.5 | 909 |
|  | 1 | 836 |
|  | 2 | 401 |
|  | 4 | 129 |
|  | 8 | 65 |
|  | 12 | 30 |
|  | 24 | 25 |
| ET-DIONE | 0 | 12 |
|  | 0.25 | 3033 |
|  | 0.5 | 2563 |
|  | 1 | 1649 |
|  | 2 | 674 |
|  | 4 | 209 |
|  | 8 | 99 |
|  | 12 | 41 |
|  | 24 | 23 |

From the data summarized in Table 1, it can be seen that administration of ET-dione via the oral route led to significantly higher amounts of alpha-ET during the early time period of from 15 minutes to approximately 1 hour after administration of the steroids; the blood levels declined rapidly in the next 1 to 2 hours, followed by a second slower phase. The half-life of the elimination in this second phase is similar to those determined for the blood levels of alpha-ET in conjugated form (presumably with sulfates and/or glucuronides). Analysis shows that, at 30 minutes post-administration, the levels of conjugated alpha-ET were 2-5 times higher than the free alpha-ET levels; this ratio increased at four hours due to the initially shorter half-life of the free drug.

At four hours post-administration, the free alpha-ET levels from ET-dione were significantly higher than from alpha-ET or beta-ET administration, indicating that ET-dione can provide a reservoir for sustained alpha-ET levels.

The present invention is further described below by reference to specific examples, which are intended to illustrate certain features of active agent administration.

Example 1: Weight gain in C57BL/6 genetically diabetic and obese mice fed alpha-ET, beta-ET or ET-dione Inhibition of the development of obesity was studied in two mutant mouse strains used for diabetes evaluation: C57BL/6, C3HeB/FeJ ($A^{vy}/A$). Four-week old C57BL/6 and $A^{vy}/A$ mice were fed alpha-ET or ET-dione in order to evaluate their effects on diabetes and obesity. C57BL/6 mice (Jackson Laboratories, Bar Harbor, ME) display the genetic obesity syndrome markers obese (ob) and diabetes (db) $A^{vy}/A$ mice (Jackson Laboratories, Bar Harbor, ME) are characterized by mild obesity and an enhanced susceptibility to certain tumors. The data are summarized below in Tables 2 and 3.

TABLE 2

| WEIGHT GAIN IN C57BL/6 MICE (grams) | | | |
|---|---|---|---|
| TREATMENT | 2 WKS | 4 WKS | 8 WKS |
| Expt. 1 | | | |
| None | 13.0 | 19.0 | 25.6 |
| Alpha-ET 0.1% | 9.9 | 14.8 | 22.1 |
| Beta-ET 0.1% | 6.5 | 12.1 | 19.6 |
| Expt. 2 | | | |
| None | 9.9 | 15.4 | 22.9 |
| ET-dione 0.4% | 5.0 | 11.6 | 17.3 |

TABLE 3

| WEIGHT GAIN IN $A^{vy}/A$ MICE (grams) | | | |
|---|---|---|---|
| TREATMENT | 2 WKS | 4 WKS | 8 WKS |
| Expt. 1 | | | |
| None | 9.2 | 18.2 | 26.9 |
| Alpha-ET 0.1% | 3.7 | 7.4 | 11.9 |
| Beta-ET 0.1% | 5.7 | 9.5 | 14.7 |
| Expt. 2 | | | |
| None | 11.2 | 18.1 | 26.6 |
| ET-dione 0.4% | 4.0 | 7.9 | 12.9 |

Groups of 8 male $A^{vy}/A$ mice; mice fed ET-dione received 0.2% for 6 days during week 4 and were then returned to the 0.4% dose level.

In C57BL/6 mice, 0.1% alpha-ET and 0.1% beta-ET reduced weight gain from controls. ET-dione, at 0.4%, ingested for 8 weeks, reduced weight gain in a manner similar to alpha- or beta-ET as shown above in Table 2. Similar results were obtained in obese $A^{vy}/A$ mice. 0.4% ET-dione was again comparable in effectiveness to 0.1% alpha- and beta-ET (Table 3).

Example 2: Effects of ET-dione and alpha-ET on weight gain in normal rats

Normal male Sprague-Dawley rats (Charles River Breeding Laboratory, Wilmington, MA) with an initial weight of 260±3 gms were allowed free access to a diet formulated to promote rapid weight gain (corn starch 15%, sucrose 15%, casein 20%, corn oil 5%, cellulose 5%, mineral mix 3.5%, vitamin mix 1%, DL-methionine 0.3%, and choline bitartrate 0.2%). Groups of ten rats were treated for three weeks with ET-dione, 0.367%, or alpha-ET, 0.2%, mixed in the diet or with diet alone. Food consumption and body weight were measured weekly. Blood samples were taken at the end of the study for assay of alpha-ET by RIA and measurement of serum total cholesterol, HDL-cholesterol and triglycerides. Liver weight (absolute and % of body weight), total cholesterol, % of esterified cholesterol and triglycerides in the liver were also determined. In addition, epididymal fat pad weights were measured.

The results are summarized below in Tables 4 and 5.

alpha-ET treated group was also lower. The weight of the epididymal fat pads was significantly lower in alpha-ET treated rats but not in ET-dione treated rats (Table 4).

Both ET-dione and alpha-ET reduced food consumption (Table 5) in this animal; the food efficiency for ET-dione was still somewhat lower than controls (0.217 vs 0.236 gms body weight per gm food intake) and, again, superior to alpha-ET. The blood levels of alpha-ET produced by 0.2% alpha-ET and 0.367% ET-dione were similar (1590 and 1750 mcg per dl, respectively). Since the blood was drawn after a fasting period of 8 to 10 hours, the measured levels are likely to be substantially lower than the average circulating levels during the study period.

A second study was carried out on male Sprague-

TABLE 4

WEIGHT GAIN IN SPRAGUE-DAWLEY RATS FED ALPHA-ET OR ET-DIONE

| Day | CONTROL | | Alpha-ET 0.2% | | ET-dione 0.367% | |
|---|---|---|---|---|---|---|
| | Weight (g) | G (g)++ | Weight (g) | G (g) | Weight (g) | G (g) |
| 0 | 260 ± 3* | — | 260 ± 3 | — | 260 ± 3 | — |
| 7 | 308 ± 5 | 48 | 301 ± 6 | 41 | 298 ± 2 | 38 |
| 14 | 354 ± 6 | 94 | 342 ± 8 | 82 | 341 ± 3 | 81 |
| 21 | 381 ± 7 | 121 | 368 ± 9 | 108 | 361 ± 3 | 101+ |
| % G vs Control Day 21 | — | | −10.8% | | −16.6% | |
| Fat Pad Wt (g) | 3.88 ± 0.29% | | 3.06 ± 0.26+ | | 3.50 ± 0.26 | |
| Fat Pad as % of Body Wt | 1.02 ± 0.08 | | 0.83 ± 0.04+ | | 0.97 ± 0.07 | |
| Alpha-ET Blood Level (ng/dl)** | 35 | | 1590 | | 1750 | |

*Mean weight in grams ± S.E.
**Measured by RIA; sample taken at sacrifice (following a non-feeding period).
+Significantly different from control (p 0.05)
++G = Weight gain.

TABLE 5

FOOD CONSUMPTION BY SPRAGUE-DAWLEY RATS FED ALPHA-ET OR ET-DIONE
FOOD CONSUMPTION (g/rat/day)

| WEEK | CONTROL | Alpha-ET 0.2% | ET-dione |
|---|---|---|---|
| 1 | 26.8 ± 0.8* | 24.7 ± 0.8 | 23.0 ± 0.6 |
| 2 | 24.9 ± 0.6 | 22.6 ± 0.9 | 24.6 ± 0.5 |
| 3 | 25.0 ± 0.6 | 23.1 ± 0.8 | 22.6 ± 0.5 |
| Average | 25.6 ± 0.6 | 23.5 ± 0.6 | 23.4 ± 0.6** |
| Food Efficiency+ | 0.236 | 0.230 | 0.217 |

*Mean ± S.E.
**Significantly different from Control (p 0.05)
+Total weight gained (g) - food consumed (g) during study Treatment with 0.367% ET-dione resulted in a significantly lower weight gain than in controls (101 g vs 121 g) during the three weeks. The weight gain of the 0.2%

Dawley rats with initial starting weight of 272±5 gms. Diet was modified to increase the fat content as follows: corn starch 19.4%, sucrose 34.6%, casein 22.2%, corn oil 8.9% lard 8.9%, mineral mix 3.5%, vitamin mix 2.2%, DL-methionine 0.3%. Groups of nine rats were treated for five weeks with diet alone, with the addition of alpha-ET at 0.2 or 0.4%, or ET-dione at 0.4 or 0.8%. On the last day of the study, the animals were dosed with approximately 1 micro Ci of $^3$H labeled material (Amersham, Arlington Heights, IL) corresponding to the treatment they had received. Groups of three animals were sacrificed at 1 hour, 4 hours and 12 hours after dosing, and the adrenals, gonads, liver, epididymal fat pads, and blood collected for analysis. Urine and feces were also collected during the post-tracer dosing period. The data is presented below in Table 6.

TABLE 6

BODY WEIGHT GAINS & FOOD CONSUMPTION IN SPRAGUE-DAWLEY RATS TREATED WITH ALPHA-ET OR ET-DIONE

| Day | Control | 0.4% Et-Dione | 0.8% ET-Dione | 0.2% Alpha-ET | 0.4% Alpha-ET |
|---|---|---|---|---|---|
| 7 | 56 | 44 | 34 | 51 | 49 |
| 14 | 109 | 89 | 83 | 100 | 98 |
| 21 | 145 | 117 | 112 | 130 | 130 |
| 28 | 183 | 149 | 144 | 165 | 162 |
| % W vs Control Day 28 | — | −18.6% | −21.3% | −9.8% | −11.5% |

FOOD CONSUMPTION (g/day)

| Week | Control | 0.4% ET-Dione | 0.8% ET-Dione | 0.2% Alpha-ET | 0.4% Alpha-ET |
|---|---|---|---|---|---|

TABLE 6-continued

| | | | | | |
|---|---|---|---|---|---|
| 1 | 25.4 ± 0.4 | 23.1 ± 0.7 | 20.4 ± 0.8 | 24.1 ± 0.4 | 23.5 ± 0.7 |
| 2 | 23.2 ± 0.8 | 21.4 ± 1.2 | 20.9 ± 0.9 | 20.9 ± 0.7 | 21.2 ± 0.5 |
| 3 | 23.3 ± 0.7 | 21.3 ± 1.0 | 19.9 ± 0.7 | 20.4 ± 0.6 | 20.8 ± 0.5 |
| 4 | 22.7 ± 1.0 | 22.3 ± 1.4 | 21.1 ± 0.6 | 21.3 ± 0.7 | 20.8 ± 0.8 |
| Av. Wks 1-4 | 23.4 | 22.0 | 20.6 | 21.7 | 21.6 |
| Food Efficiency | 0.279 | 0.250 | 0.272 | 0.272 | 0.268 |

ET-dione at 0.4% and alpha-ET at 0 2% produced reductions in weight gains ET-dione was almost twice as effective as alpha-ET at all concentrations tested. In addition, ET-dione was equally effective as alpha-ET in reducing food consumption The higher doses of ET-dione and alpha-ET did not produce substantial further decreases (Table 6).

Example 3: Effect of ET-dione treatment in diabetic mice

Eighteen C57BL/K db/db mice were divided into three groups of 5 and one group (control) of 3. This mouse strain is more diabetic and more resistant to weight gain reduction than the mouse species used in Example 1. The mice were weighed and then permitted to consume a commercially-available chow and water ad librium over a six-week study period. At the end of each week, the mice were reweighed and their blood sugar determined. The chow supplied to three of the groups had ET-dione admixed therewith at either a 0.4, 0.6 or 0 8% concentration. The data developed during this study is set forth in Table 7 below.

TABLE 7

ET-Dione Treatment in C57BL/K Diabetic Mice

| Treatment | Body Weight (g) | | | | | | |
|---|---|---|---|---|---|---|---|
| | Start | 1 | 2 | 3 | 4 | 5 | 6 |
| Chow | 17.3 ± 3.1 | 25.5 ± 3.1 | 33.3 ± 2.3 | 39.6 ± 1.6 | 43.1 ± 1.2 | 46.7 ± 1.0 | |
| 5 wk gain | | | | | | 29.4 g | |
| 0.4% ET-dione | 19.6 ± 1.8 | 26.7 ± 1.7 | 29.8 ± 1.2 | 34.4 ± 0.83 | 36.5 ± 0.8 | 42.2 ± 1.0 | 45.7 ± 0.7 |
| 6 wk gain | | | | | | | 26.1 g |
| 0.6% Et-dione | 18.1 ± 1.6 | 23.7 ± 1.9 | 27.3 ± 1.8 | 31.9 ± 1.9 | 34.7 ± 1.9 | 39.1 ± 1.6 | 42.2 ± 0.9 |
| 6 wk gain | | | | | | | 24.1 g |
| 0.8% ET-dione | 18.1 ± 1.0 | 23.3 ± 0.7 | 26.4 ± 0.6 | 31.1 ± 0.76 | 33.5 ± 0.91 | 37.0 ± 0.9 | 39.8 ± 1.2 |
| 6 wk gain | | | | | | | 21.7 g |

| | Blood Sugar | | | | | | |
|---|---|---|---|---|---|---|---|
| | Start | 1 | 2 | 3 | 4 | 5 | 6 |
| Chow | — | 167 ± 24.3 | 262 ± 22 | 277 ± 15 | 333 ± 19 | 382 ± 19 | |
| 0.4% ET-dione | — | 149 ± 3.9 | 156 ± 8.3 | 151 ± 6.3 | 148 ± 5.6 | 148 ± 17.2 | 168 ± 24.5 |
| 0.6% ET-dione | — | 143 ± 9.0 | 124 ± 10.7 | 151 ± 11.5 | 152 ± 3.7 | 159 ± 17 | 195 ± 37 |
| 0.8% ET-dione | — | 128 ± 5.0 | 126 ± 6.8 | 147 ± 4.2 | 148 ± 3.7 | 137 ± 6.7 | 184 ± 31 |

The data in Table 7 shows that ET-dione reduced the six-week weight gain which represents an excellent result in view of the difficulty in reducing weight gain in these particular mice. The data also shows that the blood sugar level in the untreated mice was dangerously high while the ET-dione had maintained the blood sugar level at an excellent level which was roughly half that of the untreated mice.

Various changes and modifications can be made in the invention described above without departing from the spirit and scope of the invention. The embodiments described herein were set forth for the purpose of illustration only.

What is claimed is:

1. A method of ameliorating the consequences of a steroid biosynthetic defect in an individual having Prader-Willi Syndrome which comprises administering to said individual an amount of at least one 3-oxo or hydroxy substituted 5-beta-androstan-17-one effective to cause normal etiocholanolone plasma levels.

2. The method of claim 1, in which the 3 substituent is oxo.

3. The method of claim 2, wherein the amount is about 0.1-100 mg/kg/day.

4. The method of claim 3, wherein the amount is about 1-10 mg/kg/day.

5. The method of claim 1, in which the 3 substituent is alpha-hydroxy.

6. The method of claim 5, wherein the amount is about 0.1-100 mg/kg/day.

7. The method of claim 6, wherein the amount is about 1-10 mg/kg/day.

8. The method of claim 1, in which the 3 substituent is beta-hydroxy.

9. The method of claim 8 wherein the amount is about 0.1-100 mg/kg/day.

10. The method of claim 9 wherein the amount is about 1-10 mg/kg/day.

11. The method of claim 1, wherein the amount is about 0.1-100 mg/kg/day.

12. The method of claim 11, wherein the amount is about 1-10 mg/kg/day.

* * * * *